United States Patent [19]

Godfrey, Jr. et al.

[11] Patent Number: 4,636,560
[45] Date of Patent: Jan. 13, 1987

[54] AMINO THIOL PEPTIDES

[75] Inventors: Jollie D. Godfrey, Jr., Trenton; Eric M. Gordon, Pennington; Norma G. Delaney, Princeton, all of N.J.

[73] Assignee: E. R. Squibb & Sons, Inc., Princeton, N.J.

[21] Appl. No.: 672,044

[22] Filed: Nov. 16, 1984

[51] Int. Cl.$^4$ .................. C07K 5/506; C07K 5/508
[52] U.S. Cl. ...................... 530/331; 530/800
[58] Field of Search ............................. 514/2

[56] References Cited

U.S. PATENT DOCUMENTS 4,500,518  2/1985  Gordon ....................... 514/2

OTHER PUBLICATIONS

H. Umezawa et al., J. Antibiotics, vol. 29, p. 97 (1976).
H. Suda et al., J. Antibiotics, vol. 29, p. 100 (1976).
T. Aoyagi et al., J. Antibiotics, vol. 31, p. 636 (1978).
H. Tobe et al., Agric. Biological Chemistry, vol. 43, p. 591 (1979).
G. W. Wagner et al., J. Neurochem., vol. 37, p. 709 (1980).
Chan, W.-C., Biochemical and Biophysical Res. Comm., vol. 116, p. 297 (1983).

*Primary Examiner*—Delbert R. Phillips
*Attorney, Agent, or Firm*—Lawrence S. Levinson; Donald J. Barrack

[57] ABSTRACT

Analgesic and hypotensive activity is exhibited by compounds having the formula

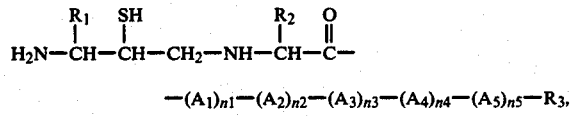

$-(A_1)_{n1}-(A_2)_{n2}-(A_3)_{n3}-(A_4)_{n4}-(A_5)_{n5}-R_3,$ and pharmaceutically acceptable salts thereof, wherein
$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;
$R_3$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;
$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

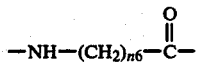

wherein $n_6$ is an integer of 2 to 15;
$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and
$n_1$, $n_2$, $n_3$, $n_4$ and $n_5$ each is independently 0 or 1.

6 Claims, No Drawings

AMINO THIOL PEPTIDES

RELATED APPLICATION

U.S. patent application Ser. No. 602,030, filed Apr. 19, 1984, now U.S. Pat. No. 4,500,518, issued Feb. 19, 1985, discloses acylated amino thiol dipeptides having the formula

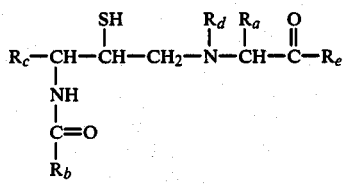

wherein $R_a$ is hydrogen, alkyl, or specified substituted alkyl groups, $R_b$ is selected from specified substituted alkyl, aryl and heteroaryl groups, $R_c$ is hydrogen, alkyl or specified substituted alkyl groups, $R_d$ is hydrogen, alkyl, cycloalkyl or specified substituted alkyl groups, and $R_e$ is selected from specified amino and imino acids. The compounds are angiotensin converting enzyme inhibitors and are useful as hypotensive agents.

U.S. patent application Ser. No. 628,004, filed July 5, 1984 now U.S. Pat. No. 4,552,866, issued Nov. 12, 1985, discloses diamino alcohols having the formula

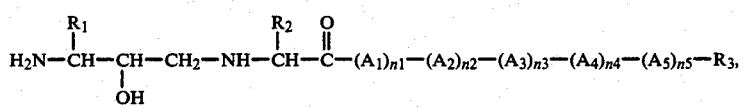

wherein the variables are as described hereinafter, which can be used as analgesics.

BRIEF DESCRIPTION OF THE INVENTION

Compounds having the formula

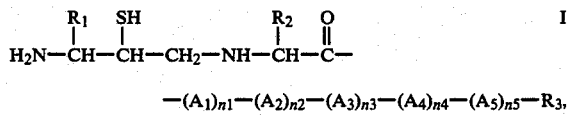

and pharmaceutically acceptable salts thereof, possess aminopeptidase inhibitory activity, and can be used as analgesics. In formula I, and throughout the specification, the symbols are as defined below.

$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

$R_3$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;

$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tryosyl, leucyl, valyl, aspartyl, prolyl, norleucyl, norvalyl, or

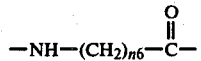

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and $n_1$, $n_2$, $n_3$, $n_4$ and $n_5$ each is independently 0 or 1.

The terms "alkyl" and "alkoxy", as used throughout the specification either individually or as part of a larger group, refer to straight and branched chain groups having 1 to 7 carbon atoms.

The term "halo substituted alkyl", as used throughout the specification either individually or as part of a larger group, refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl", as used throughout the specification either individually or as part of a larger group, refers to cycloalkyl groups having 3, 4, 5, 6 or 7 carbon atoms.

The term "substituted alkyl", as used throughout the specification, either individually or as part of a larger group, refers to alkyl groups substituted with one, or more (preferably one), hydroxy or $-NY_3Y_4$ groups, wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

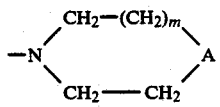

and A is CH—Q, oxygen, or N—Q, Q is hydrogen or alkyl and m is 0 or 1.

The term "heteroaryl", as used throughout the specification either individually or as part of a larger group, refers to 2- or 3-furanyl, 2- or 3-thienyl, 2-, 3- or 4-pyridinyl, 4-imidazolyl and 3-indolyl.

The term "aryl", as used throughout the specification either individually or as part of a larger group, refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie as an analgesic agent due to their ability to inhibit an enkephalin-degrading aminopeptidase.

It is well known that the weak and shortlasting analgesic activity of endogenous enkephalins can be attributed to their rapid inactivation. Enkephalins are metabolized by several hydrolytic enzymes present in the brain: (1) aminopeptidases release the $Tyr^1$ residue, (2) a dipeptidyl aminopeptidase releases the $Tyr^1$-$Gly^2$ residue and (3) two enzymes cleave the penultimate $Gly^3$-$Phe^4$ bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism.

The compounds of this invention inhibit the aminopeptidase activity and thus act as analgesic agents.

Those compounds of formula I, and pharmaceutically acceptable salts thereof, wherein $R_2$ is a lipophilic sidechain, especially arylalkyl (e.g., benzyl) exhibit inhibitory activity against enkephalin cleaving endopeptidase in addition to the above-described aminopeptidase activity.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

The compounds of this invention can be prepared by coupling an aldehyde having the formula

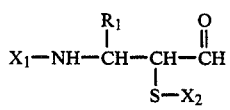  II with a peptide ester having the formula

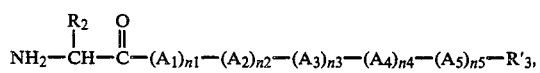  III wherein $X_1$ is an amino protecting group (such as t-butoxycarbonyl or benzyloxycarbonyl), $X_2$ is a sulfur protecting group (such as p-methoxybenzyl) and $R'_3$ is a carboxy protecting group, alkoxy, (substituted alkyl)oxy or $-NY_1Y_2$, and chemically reducing the resulting compound (using, for example, sodium borohydride) to yield the corresponding compound having the formula

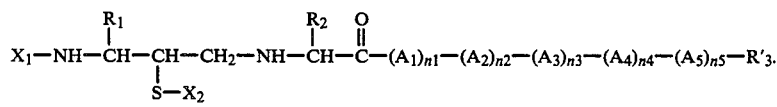  IV

Deprotection of a compound of formula IV to obtain the corresponding product of formula I (wherein $R_3$ is other than hydroxy) can be accomplished using art-recognized procedures. The particular deprotection reactions used will, of course, depend on the particular protecting groups present.

Those products of formula I wherein $R_3$ is hydroxy can be obtained from a corresponding product of formula I wherein $R_3$ is a cleavable carboxyl protecting group such as t-butyl or benzylhydryl. Here again, art-recognized techniques are employed to accomplish a deprotection reaction.

The aldehyde reactant of formula II can be obtained by first treating an activated form (preferably a mixed anhydride) of an N-protected amino acid having the formula

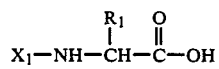  V with diazomethane to yield a compound having the formula

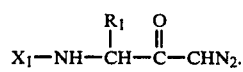  VI

Treatment of a diazoketone of formula VI in methanol with silver benzoate and triethylamine yields a compound having the formula

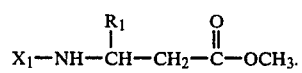  VII

Treatment of a compound of formula VII with lithium diisopropylamide and a disulfide having the formula

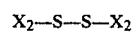  VIII at a reduced temperature yields the corresponding compound having the formula

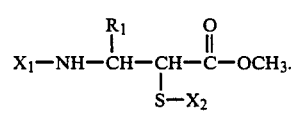  IX

Reduction of the esterified carboxyl group of formula IX to the corresponding alcohol having the formula

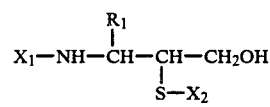  X can be accomplished by treating a compound of formula IX with lithium chloride and sodium borohydride. Conversion of an alcohol of formula X to the corresponding aldehyde of formula II can be accomplished by treatment with sulfur trioxide pyridine complex and dimethylsulfoxide in the presence of diisopropylethylamine.

The compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, (e.g., camphorsulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

The compounds of formula I wherein $R_3$ is hydroxy form basic salts with a variety of inorganic and organic bases. The pharmaceutically acceptable salts include alkali metal salts such as sodium or potassium, alkaline earth metal salts such as calcium or magnesium, and salts derived from amino acids such as arginine, lysine, etc. The salts can be prepared by reacting the acid form of the compound, i.e., $R_3$ is hydroxy, with an equivalent of the base supplying the desired basic ion in a medium in which the salt precipitates or in aqueous medium and then lyophilizing.

In the compounds of formula I, the carbon atom to which the mercapto group is attached is asymmetric and the carbon atom to which the $R_1$ or $R_2$ substituent is attached will also be asymmetric if $R_1$ or $R_2$ is other than hydrogen. The compounds, therefore, may exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques. The amino acids designated $A_1$, $A_2$, $A_3$, $A_4$ and $A_5$ may be in the L or D configuration.

The following example is a specific embodiment of this invention.

EXAMPLE 1

N-[N-(3-Amino-2-mercapto-4-phenylbutyl)-L-phenylalanyl]-L-leucine (A) (S)-3-Diazo-2-oxo-1-(phenylmethyl)carbamic acid, 1,1-dimethylethyl ester To a solution of N-(t-butoxycarbonyl)-L-phenylalanine (47.75 g, 0.18 mole) and N-methylmorpholine (19.8 ml, 0.18 mole) in dry tetrahydrofuran (300 ml) at −20° C. under argon was added over a 5 minute period isobutyl chloroformate (23.4 ml, 0.18 mole). After stirring for 20 minutes at −20° C., the N-methylmorpholine hydrochloride was removed by filtration and the filter cake was washed with a small portion of cold tetrahydrofuran. The filtrate was treated with a cold (0° C.), ethereal solution of diazomethane (~270 mmol, prepared from 64.2 g of Diazald and distilled). After stirring at 0° C. for 30 minutes, the mixture was warmed to room temperature. After stirring for 2.5 hours, the excess diazomethane was removed by bubbling a stream of argon through the reaction mixture for 1 hour. The bulk of the solvent was removed at reduced pressure and the residue was dissolved in ethyl acetate. The resulting solution was washed with water (twice), 0.25M citric acid (twice), 1N sodium bicarbonate, and brine. After drying over anhydrous magnesium sulfate, the solvent was removed at reduced pressure and the residue was dissolved in isopropyl ether and placed in the cold (−5° C.). The resulting crystals were collected by filtration and washed with hexane to give (S)-3-diazo-2-oxo-1-(phenylmethyl)carbamic acid, 1,1-dimethylethyl ester as a bright yellow solid: 33.96 g, $R_f$=0.21 (silica gel, hexane:ethyl acetate, 3:1). The mother liquors yielded an additional 7.45 g of (S)-3-diazo-2-oxo-1-(phenylmethyl)carbamic acid, 1,1-dimethylethyl ester.

(B) (S)-3-[[(1,1-Dimethylethoxy)carbonyl]amino]benzenebutanoic acid, methyl ester To a solution of (S)-3-diazo-2-oxo-1-(phenylmethyl)carbamic acid, 1,1-dimethylethyl ester (5.36 g, 18.52 mmol) in methanol (50 ml) was added 5.0 ml of a solution of silver benzoate (1.0 g) in triethylamine (10 ml). After nitrogen evolution had ceased, an additional 0.2 ml of the silver benzoate/triethylamine solution was added. After stirring for 15 minutes, the reaction mixture was treated with activated charcoal and filtered through Celite using ethyl acetate. The filtrate was concentrated at reduced pressure and the residue was dissolved in ethyl acetate and washed with water (twice), 1N sodium bicarbonate (twice), 1N hydrochloric acid (twice), 1N sodium bicarbonate and brine. After drying over anhydrous magnesium sulfate, the solvent was removed at reduced pressure and the residue chromatographed (flash, silica gel; benzene:isopropyl ether, 87.5:12.5) to give (S)-3-[[(1,1-dimethylethoxy)carbonyl]amino]benzenebutanoic acid, methyl ester as a colorless solid: 4.33 g; $[\alpha]_d^{20}$=−19.2° (c=1.06, methanol; $R_f$=0.31 (silica gel, benzene:ethyl acetate, 9:1).

(C) (3S)-3-[[(1,1-Dimethylethoxy)carbonyl]amino]2-[[(4-methoxyphenyl)methyl]thio]benzenebutanoic acid, methyl ester To a solution of freshly distilled diisopropylamine (2.10 ml, 15 mmol) in anhydrous tetrahydrofuran (20 ml) at 0° C. under argon was added a hexane solution of n-butyl lithium (6.10 ml of a 2.40M solution, 14.65 mmol). After stirring at 0° C. for 30 minutes, the resulting solution of lithium diisopropylamide was cooled to −78° C. and a solution of (S)-3-[[(1,1-dimethylethoxy)carbonyl]amino]benzenebutanoic acid, methyl ester (2.0 g, 6.81 mmol) in dry tetrahydrofuran (8 ml) was added dropwise over a period of 5 minutes. After stirring at −78° C. for 15 minutes, a solution of p-methoxybenzyl disulfide (2.50 g, 8.18 mmol) in dry tetrahydrofuran (9 ml) was added. After 5 minutes at −78° C., the mixture was warmed to 0° C. and stirring continued for 45 minutes. The reaction was quenched with 1N hydrochloric acid and diluted with ethyl acetate. The resulting solution was washed with water, 1N hydrochloric acid, 1N sodium bicarbonate, and brine. After drying over anhydrous magnesium sulfate, the solvent was removed at reduced pressure and the residue chromatographed (flash, silica: benzene:isopropyl ether, 92:8) to give (3S)-3-[[(1,1-dimethylethoxy)carbonyl]amino]-2-[[(4-methoxyphenyl)methyl]thio]benzenebutanoic acid, methyl ester as a colorless oil: 1.89 g, $R_f$=0.54 (silica gel, benzene:isopropyl ether, 4:1).

(D) (1S)-[3-Hydroxy-2-[[(4-methoxyphenyl)methyl]thio]-1-(phenylmethyl)propyl]carbamic acid, 1,1-dimethylethyl ester To a solution of (3S)-3-[[(1,1-dimethylethoxy)carbonyl]amino]-2-[](4-methoxyphenyl)methyl]thio]benzenebutanoic acid, methyl ester (1.73 g, 3.88 mmol) in tetrahydrofuran (25 ml) and absolute ethanol (25 ml) was added lithium chloride (0.66 g, 15.6 mmol) and sodium borohydride (0.59 g, 15.6 mmol). After stirring at room temperature under argon for 24 hours, the mixture was quenched with 1N hydrochloric acid and diluted with ethyl acetate. The resulting solution was washed with water, 1N hydrochloric acid (twice), 1N sodium bicarbonate, and brine. After drying over anhydrous magnesium sulfate, the solvent was removed at reduced pressure and the residue chromatographed (flash, silica gel, benzene:acetone, 92:8) to give the separated diastereomers of (1S)-[3-hydroxy-2-[[(4-methoxyphenyl)methyl]thio]-1-(phenylmethyl)propyl]carbamic acid, 1,1-dimethylethyl ester as colorless solids: Isomer A, 0.17 g, $R_f$=0.39, (silica gel, benzene:ethyl acetate, 4:1).

(E)
(1S)-[1-[Formyl[[(4-methoxyphenyl)methyl]thio]methyl]-2-phenylethyl]carbamic acid, 1,1-dimethylethyl ester A solution of pyridinium-1-sulfonate (789 mg, 3 eq) and anhydrous dimethylsulfoxide (3.0 ml) was stirred at room temperature under argon. After 15 minutes, a solution of (1S)-[3-hydroxy-2-[[(4-methoxyphenyl)methyl]thio]-1(phenylmethyl)propyl]carbamic acid, 1,1-dimethylethyl ester (690 mg, 1.65 mmol), diisopropylethylamine (1.73 ml, 6 eq) and dry dichloromethane (5.0 ml) was added in one portion. After 15 minutes longer, the reaction was diluted with ethyl acetate and washed with water, 1N hydrochloric acid, 1N sodium bicarbonate, brine and dried over anhydrous magnesium sulfate. Concentration of the filtrate yielded (1S)-[1-[formyl[[(4-methoxyphenyl)methyl]thio]methyl]-2-phenylethyl]carbamic acid, 1,1-dimethylethyl ester as a yellow solid: 610 mg (1.47 mmol); $R_f$=0.59 (silica gel, benzene:ethyl acetate 4:1).

(F)
N-[N-[(3S)-3-[[(1,1-Dimethylethoxy)carbonyl]amino]-2-[[(4-methoxyphenyl)methyl]thio]-4-phenylbutyl]-L-phenylalanyl]-L-leucine, 1,1-dimethylethyl ester A mixture of (1S)-[1-[formyl[[(4-methoxyphenyl)methyl]thio]methyl]-2-phenylethylcarbamic acid, 1,1-dimethylethyl ester (550 mg, 1.3 mmol), L-phenylalanyl-L-leucine-t-butyl ester (886 mg, 2 eq), crushed 3A sieves (1.5 g) and anhydrous benzene (15 ml) was stirred at room temperature under argon for 105 minutes. The mixture was diluted with ethyl acetate and passed through a pad of Celite to remove sieves. Concentration of the filtrate yielded a yellow oil which was dissolved in anhydrous ice cold methanol (15 ml) and placed in a 0° C. bath. To the solution was added sodium borohydride (100 mg, 2 eq). After 30 minutes, more sodium borohydride (100 mg) was added. After 30 minutes, the reaction mixture was quenched with 1N hydrochloric acid (10 ml), diluted with ethyl acetate and washed with water (twice), 1N hydrochloric acid (twice), 1N sodium bicarbonate, brine and dried over anhydrous magnesium sulfate. Evaporation of the solvent yielded a nearly colorless oil. The oil was chromatographed (flash, silica gel, benzene:acetone 95:5) to yield N-[N-[(3S)-3-[[(1,1-dimethylethoxy)carbonyl]amino]-2-[[(4-methoxyphenyl)methyl]thio]-4-phenylbutyl-[L-phenylalanyl]-L-leucine, 1,1-dimethylethyl ester as a slightly yellow oil: 780 mg (1.06 mmol); $R_f$=0.38 Isomer A, $R_f$=0.33 Isomer B (silica gel, benzene:ethyl acetate 4:1).

(G)
N-[N-(3-Amino-2-mercapto-4-phenylbutyl)-L-phenylalanyl]-L-leucine

A solution of N-[N-[(3S)-3-[[(1,1-dimethylethoxy)carbonyl]amino]-2-[[(4-methoxyphenyl)methyl]thio]-4-phenylbutyl]-L-phenylalanyl]-L-leucine, 1,1-dimethylethyl ester (780 mg, 1.06 mmol), anisole (1.0 ml) and trifluoroacetic acid (14 ml) was stirred at room temperature under argon. After 1 hour, the reaction was cooled to 0° C. and mercuric trifluoroacetate (497 mg, 1.1 eq) was added. The reaction was stirred for 1 hour at 0° C. and then concentrated to a red oil. The oil was triturated with ether/hexane and a nearly colorless solid was collected and washed with hexane. The solid was dissolved in degassed 80% aqueous acetic acid (20 ml) and hydrogen sulfide was bubbled through the solution for 30 minutes. The black reaction mixture was filtered through a pad of Celite followed by a Millipore filter (Teflon). The filtrate was concentrated to an amber oil. The oil was diluted with degassed double distilled water (20 ml) and 1N hydrochloric acid (3.2 ml, 1.5 eq) and the mixture filtered (Millipore, Metricel). The clear, colorless filtrate was lyophilized and relyophilized twice from water to yield the title compound as a fluffy, colorless solid: 490 mg (0.87 mmol); $R_f$=0.70 (silica gel, N-butanol:water:acetic acid, 4:1:1); $R_f$=0.75 (silica gel, chloroform:methanol:acetic acid, 4:1:1); fast atom bombardment mass spectrum: $(M+H)^+$ m/e=458, $(M-H)^-$ m/e=456; melting point 123°-160° C.; $[\alpha]_D$=−12.8° (c=1.23, methanol). Analysis: $C_{25}H_{35}N_3O_3S$.1.8 mole HCl.2.2 mole $H_2O$: C, 53.34; H, 7.38; N, 7.46; S, 5.69; SH 5.87; Cl, 11.33. Found: C, 53.06; H, 7.15; N, 7.12; S, 5.39; SH, 5.86; Cl, 11.08.

The following additional compounds fall within the scope fo this invention.

$$H_2N-\underset{R_1}{CH}-\underset{SH}{CH}-CH_2-NH-\underset{R_2}{CH}-\underset{O}{\overset{\parallel}{C}}-(A_1)_{n1}-(A_2)_{n2}-(A_3)_{n3}-(A_4)_{n4}-(A_5)_{n5}-R_3,$$

| $R_1$ | $R_2$ | $-(A_1)_{n1}-(A_2)_{n2}-(A_3)_{n3}-(A_4)_{n4}-(A_5)_{n5}-R_3$ |
|---|---|---|
| —CH$_2$CH(CH$_3$)$_2$ | —CH$_2$CH(CH$_3$)$_2$ | —Val—OCH$_3$ |
| —CH$_2$CH(CH$_3$)$_2$ | —CH$_2$CH(CH$_3$)$_2$ | —Phe—NH$_2$ |
| —CH$_2$CH(CH$_3$)$_2$ | —(CH$_2$)$_4$NH$_2$ | —OH |
| —CH$_2$CH(CH$_3$)$_2$ | —(CH$_2$)$_3$NHC(=NH)—NH$_2$ | —NH$_2$ |
| 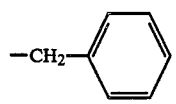 | 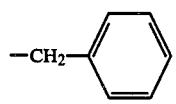 | —NH$_2$ |

-continued

| $R_1$ | $R_2$ | $-(A_1)_{n1}-(A_2)_{n2}-(A_3)_{n3}-(A_4)_{n4}-(A_5)_{n5}-R_3$ |
|---|---|---|
| $-CH_2-C_6H_5$ | $-(CH_2)_4NH_2$ | $-OH$ |
| $-CH_2-C_6H_5$ | $-(CH_2)_3NHC(=NH)NH_2$ | $-OH$ |
| $-CH_2-C_6H_4-OH$ | $-H$ | $-OH$ |
| $-CH_2-C_6H_4-OH$ | $-CH_3$ | $-Gly-Phe-Leu-NH_2$ |
| $-CH_2OH$ | $-CH_2OH$ | $-NH_2$ |
| $-CH_2OH$ | $-CH_2OH$ | $-Ala-OH$ |
| $-(CH_2)_4NH_2$ | $-(CH_2)_4NH_2$ | $-NH_2$ |
| $-(CH_2)_4NH_2$ | $-CH_2CH(CH_3)_2$ | $-Leu-OCH_3$ |
| $-(CH_2)_4NH_2$ | $-(CH_2)_3NHC(=NH)NH_2$ | $-Ala-NH_2$ |
| $-CH_3$ | $-CH_2-C_6H_5$ | $-Leu-NH-CH_2-C_6H_5$ |
| $-(CH_2)_3NHC(=NH)NH_2$ | $-CH_2CH(CH_3)_2$ | $-Leu-OH$ |
| $-(CH_2)_3NHC(=NH)NH_2$ | $-(CH_2)_4NH_2$ | $-OH$ |
| $-(CH_2)_3NHC(=NH)NH_2$ | $-(CH_2)_4NH_2$ | $-Phe-Ala-NH_2$ |
| $-(CH_2)_4NHC(=NH)NH_2$ | $-(CH_2)CH(CH_3)_2$ | $-Ala-Ala-Gly-OH$ |
| $-(CH_2)_2CO_2H$ | $-CH_2CH(CH_3)$ | $-Ala-NH_2$ |
| $-(CH_2)_3CO_2H$ | $-CH_3$ | $-Leu-OH$ |
| $-CH_2CH(CH_3)_2$ | $-CH_2CH(CH_3)_2$ | $-Val-Phe-OCH_3$ |
| $-CH_2-C_6H_5$ | $-CH_2-C_6H_5$ | $-NH-(CH_2)_2-C(=O)-OH$ |
| $-CH_2-C_6H_5$ | $-CH_2CH(CH_3)_2$ | $-NH_2$ |
| $-CH_2-C_6H_5$ | $-CH_2CH(CH_3)_2$ | $-OH$ |
| $-CH_2CH(CH_3)_2$ | $-CH_2CH(CH_3)_2$ | $-OH$ |

-continued

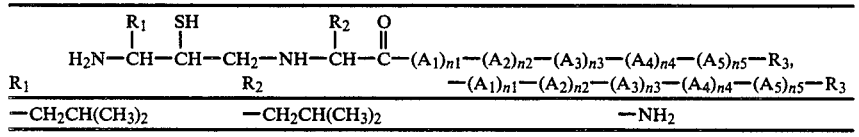

| $R_1$ | $R_2$ | $-(A_1)_{n1}-(A_2)_{n2}-(A_3)_{n3}-(A_4)_{n4}-(A_5)_{n5}-R_3$ |
|---|---|---|
| $-CH_2CH(CH_3)_2$ | $-CH_2CH(CH_3)_2$ | $-NH_2$ |

What is claimed is:

1. A compound having the formula

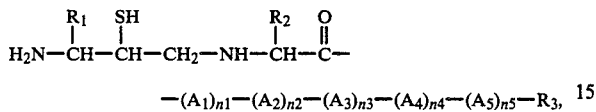

$-(A_1)_{n1}-(A_2)_{n2}-(A_3)_{n3}-(A_4)_{n4}-(A_5)_{n5}-R_3,$ and pharmaceutically acceptable salts thereof, wherein $R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

$R_3$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;

$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or $$-NH-(CH_2)_{n6}-\overset{O}{\underset{\|}{C}}-$$

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and $n_1$, $n_2$, $n_3$, $n_4$ and $n_5$ each is independently 0 or 1.

2. A compound in accordance with claim 1 wherein $n_1$ is 1 and $n_2$, $n_3$, $n_4$ and $n_5$ are each 0.

3. A compound in accordance with claim 1 wherein $R_1$ is phenylmethyl and $R_2$ is phenylmethyl.

4. A compound in accordance with claim 1 wherein $R_3$ is hydroxy.

5. A compound in accordance with claim 1 wherein $R_1$ is phenylmethyl, $R_2$ is phenylmethyl, $n_1$ is 1, $n_2$, $n_3$, $n_4$ and $n_5$ are each 0 and $R_3$ is hydroxy.

6. The compound in accordance with claim 1, N-[N-(3-amino-2-mercapto-4-phenylbutyl)-L-phenylalanyl]-L-leucine.

* * * * *

UNITED STATES PATENT AND TRADEMARK OFFICE
CERTIFICATE OF CORRECTION

PATENT NO. : 4,636,560
DATED : January 13, 1987
INVENTOR(S) : Jollie D. Godfrey, Jr. et al.

It is certified that error appears in the above-identified patent and that said Letters Patent is hereby corrected as shown below:

Column 5, line 61, delete "$-5^{\circ}$" and replace with "$\sim 5^{\circ}$".

Column 7, line 38, please add "]" after "phenylethyl" and before "carbamyl".

Column 8, line 50, correct the spelling of the word "of".

Signed and Sealed this

Fourteenth Day of April, 1987

Attest:

DONALD J. QUIGG

Attesting Officer     Commissioner of Patents and Trademarks